US008805614B2

(12) United States Patent
Andrews et al.

(10) Patent No.: US 8,805,614 B2
(45) Date of Patent: Aug. 12, 2014

(54) DOWNHOLE SAMPLE ANALYSIS METHOD

(75) Inventors: A. Ballard Andrews, Wilton, CT (US);
Oleg Zhdaneev, Bergen (NO); Oliver C. Mullins, Ridgefield, CT (US)

(73) Assignee: Schlumberger Technology Corporation, Cambridge, MA (US)

( * ) Notice: Subject to any disclaimer, the term of this patent is extended or adjusted under 35 U.S.C. 154(b) by 284 days.

(21) Appl. No.: 12/872,452

(22) Filed: Aug. 31, 2010

(65) Prior Publication Data
US 2012/0053838 A1 Mar. 1, 2012

(51) Int. Cl.
*E21B 49/00* (2006.01)
*E21B 7/00* (2006.01)
*E21B 49/10* (2006.01)
*G01N 33/543* (2006.01)
*G01N 30/02* (2006.01)

(52) U.S. Cl.
USPC ............. 702/8; 702/24; 73/19.02; 175/50; 175/57

(58) Field of Classification Search
USPC ............ 702/6, 9–13, 22–32; 73/23, 230, 152; 250/282
See application file for complete search history.

(56) References Cited

U.S. PATENT DOCUMENTS

| 4,432,706 | A  | * | 2/1984 | Gilbertson .................... 417/399 |
| 5,662,170 | A  | * | 9/1997 | Donovan et al. ............. 166/358 |
| 6,367,366 | B1 | * | 4/2002 | Bloom et al. .................. 92/5 R |
| 6,426,225 | B1 | * | 7/2002 | Lewis et al. ........................ 436/8 |
| 6,825,657 | B2 |   | 11/2004 | Kleinberg et al. |
| 7,222,022 | B2 | * | 5/2007 | Kneissl et al. .................. 702/12 |
| 7,305,306 | B2 |   | 12/2007 | Venkataramanan et al. |
| 7,384,453 | B2 |   | 6/2008 | Bostrom et al. |
| 7,520,158 | B2 |   | 4/2009 | DiFoggio |
| 7,600,413 | B2 |   | 10/2009 | Shah et al. |
| 7,637,151 | B2 |   | 12/2009 | Raghuraman et al. |
| 7,654,130 | B2 |   | 2/2010 | Shah et al. |
| 7,658,092 | B2 |   | 2/2010 | Bostrom et al. |
| 7,687,769 | B2 |   | 3/2010 | Indo et al. |
| 7,822,554 | B2 |   | 10/2010 | Zuo et al. |
| 7,996,154 | B2 |   | 8/2011 | Zuo et al. |
| 8,078,402 | B2 |   | 12/2011 | Ziauddin et al. |
| 8,141,648 | B2 | * | 3/2012 | Darnell et al. ............... 166/386 |

(Continued)

FOREIGN PATENT DOCUMENTS

WO 2011/044547 4/2011

OTHER PUBLICATIONS

S.S. Betancourt, et. al., Nanoaggregates of Asphaltenes in a Reservoir Crude Oil and Reservoir Connectivity, Energy & Fuels 2009, Amer. Chem. Soc., 23, 1178-1188 (2009).

(Continued)

*Primary Examiner* — Tung S Lau
*Assistant Examiner* — Stephanie Chang
(74) *Attorney, Agent, or Firm* — Jakub M. Michna; Bridget Laffey

(57) ABSTRACT

A method for downhole fluid analysis is disclosed. The method includes positioning a downhole fluid sampling tool at first and second locations; extracting and compositionally analyzing samples of reservoir fluid while positioned at the first and second locations; comparing analysis results; and repositioning the tool to a third location depending on the results of the comparison. The compositional analysis can be performed using downhole gas chromatography and mass spectrometry systems and preferably can identify subtle non-homogeneities such as biomarkers. The fluid extraction can be performed using a focuses dual-flowline type sampling probe.

35 Claims, 9 Drawing Sheets

(56) References Cited

U.S. PATENT DOCUMENTS

| | | | |
|---|---|---|---|
| 8,165,817 B2 | 4/2012 | Betancourt et al. | |
| 8,172,959 B2* | 5/2012 | Sakaguchi et al. | 148/327 |
| 8,271,248 B2 | 9/2012 | Pomerantz et al. | |
| 2003/0106993 A1* | 6/2003 | Chen et al. | 250/269.1 |
| 2003/0188866 A1* | 10/2003 | Bissonnette et al. | 166/278 |
| 2004/0112594 A1* | 6/2004 | Aronstam et al. | 166/249 |
| 2007/0114021 A1* | 5/2007 | Brown et al. | 166/250.1 |
| 2008/0073077 A1* | 3/2008 | Tunc et al. | 166/250.01 |
| 2008/0105032 A1 | 5/2008 | Reddy et al. | |
| 2009/0084545 A1* | 4/2009 | Banerjee et al. | 166/250.15 |
| 2009/0089028 A1* | 4/2009 | Sagert et al. | 703/6 |
| 2009/0120690 A1* | 5/2009 | Phillips | 175/45 |
| 2009/0139934 A1 | 6/2009 | Steinecker et al. | |
| 2009/0150087 A1* | 6/2009 | Steinecker | 702/24 |
| 2009/0151426 A1 | 6/2009 | Shah et al. | |
| 2009/0158815 A1 | 6/2009 | Shah et al. | |
| 2009/0158820 A1 | 6/2009 | Bostrom et al. | |
| 2009/0235731 A1* | 9/2009 | Zuo et al. | 73/152.28 |
| 2009/0288881 A1* | 11/2009 | Mullins et al. | 175/50 |
| 2009/0312997 A1 | 12/2009 | Freed et al. | |
| 2010/0282475 A1* | 11/2010 | Darnell et al. | 166/373 |
| 2011/0061935 A1* | 3/2011 | Mullins et al. | 175/50 |
| 2011/0203803 A1* | 8/2011 | Zemlak et al. | 166/349 |
| 2012/0000279 A1 | 1/2012 | Daniel et al. | |
| 2012/0232799 A1 | 9/2012 | Zuo et al. | |

OTHER PUBLICATIONS

Peters et al., "Chapter 1: Origin and preservation of organic matter," Detection of Petroleum in Prospective Reservoir Rocks, The Biomarker Guide vol. 1, Cambridge University Press: New York, 1993: pp. 3-5, 102-111.

Peters et al., "Chapter 12: Geochemical correlation and chemometrics," The Biomarker Guide vol. 2, Cambridge University Press: New York, 2005: pp. 475-482.

International Search Report and Written Opinion of PCT Application No. PCT/2011/037142 dated Feb. 9, 2012: pp. 1-9.

Mullins, "Asphaltenes and equilibrium fluid distributions" and "Compartments," The Physics of Reservoir Fluids: Discovery Through Downhole Fluid Analysis, Schlumberger: Sugar Land, 2008: pp. 15-24 and pp. 43-46.

* cited by examiner

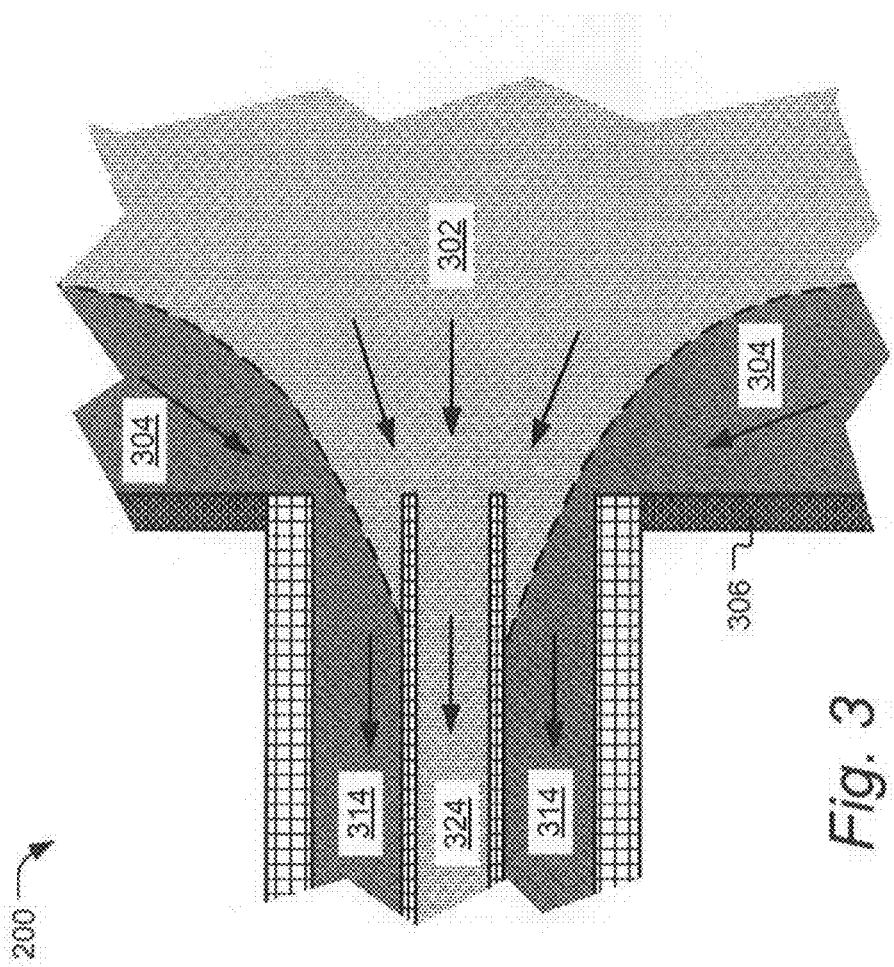
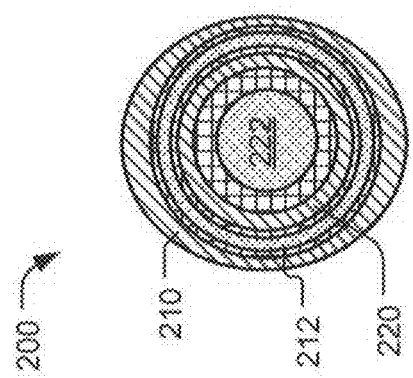
Fig. 3
Fig. 2

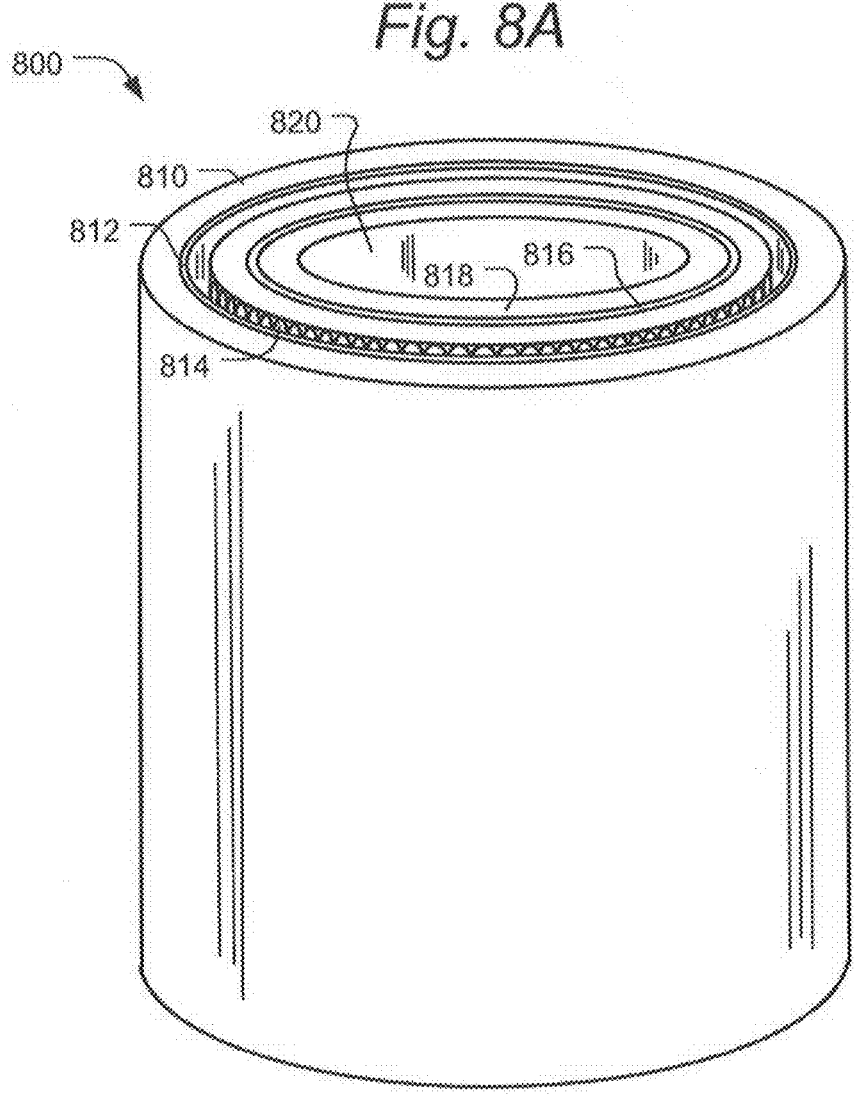
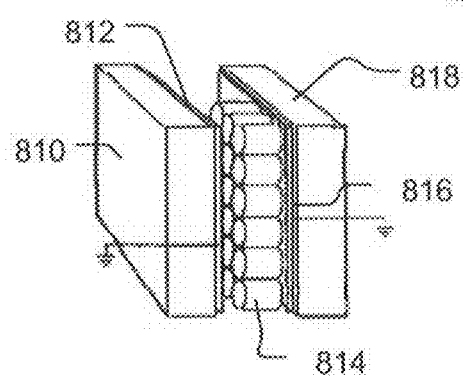

DOWNHOLE SAMPLE ANALYSIS METHOD

FIELD OF THE INVENTION

The present invention relates to the field of downhole sample analysis of reservoir fluids. More specifically, the invention relates to downhole analysis using gas chromatography in connection with focused-probe and multi flowline downhole sampling techniques.

BACKGROUND

Downhole fluid analysis (DFA) is a rapidly growing discipline in wireline logging and has become a keystone in reservoir evaluation. DFA addresses the failed and overly optimistic assumption that oil reservoirs consist of "one giant tank of homogeneous hydrocarbon." DFA can be used to find compositional gradients as well as to identify compartments. DFA also can be used to establish reservoir connectivity. DFA is typically based on bulk optical spectroscopy, which is useful to determine concentrations or ratios of components in sampled fluid.

Schlumberger has pioneered the use of optical and other spectroscopic techniques to analyze formation fluids downhole. For example, Schlumberger has introduced an optical measurement technique to estimate gas-oil ratio (GOR) of formation fluids, and determine hydrocarbon and gas composition for C1, C2-C5+, and C6+. While these advances have been impressive, it is still common practice to send samples of the formation fluids and transport them to the laboratory for further detailed analysis. Current downhole analysis techniques do not provide quantitative measurement of the individual hydrocarbon moieties for C2, C3, C4 and C5 and molecules with more that six carbons are undistinguishable.

Another challenge with DFA is the time used to extract a useful sample of reservoir fluid. Using a conventional fluid sampling probe a long time can be taken up pumping fluid until it is suitably free of filtrate contaminants. Using a focused probe, such as one with two flowlines speeds up the time needed for extractions. However, it is also desirable to speed up the process while not sacrificing spatial resolution.

SUMMARY

In accordance with some embodiments a method for downhole fluid analysis is provided. The method includes positioning a tool at first and second locations, the tool including a downhole fluid analysis system; extracting and first and second samples of reservoir fluid while positioned at the first and second locations; analyzing each sample using the downhole fluid analysis system; comparing analysis results of the first and second samples; and repositioning the tool to a third location, which depends at least in part on the comparison.

According to some embodiments the analyzing of the samples includes composition analysis. The composition analysis can include identifying hydrocarbon molecules having at least 10 carbon atoms, and preferably at least 20 carbon atoms. The composition analysis also preferably includes identifying one or more biomarkers.

The third location is preferably between the first and second locations in cases where there comparison analysis yields an substantial difference between compositions of the first and second samples.

The downhole fluid analysis system can include one or two dimensional downhole gas chromatography system, and/or a downhole mass spectrometry system.

The fluid extraction is preferably made using a sampling probe having a first flowline connected to a central probe portion and a second flowline connected to an outer guard portion surrounding the central probe portion.

According to some embodiments the tool is a wireline tool; and according to some other embodiments the tool is a logging while drilling tool.

Further features and advantages will become more readily apparent from the following detailed description when taken in conjunction with the accompanying Drawings.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIGS. 2 and 3 illustrate features of a focused probe used for downhole fluid sampling, according to some embodiments;

FIGS. 8A-B illustrate an ion pump for used in downhole mass spectrometry, according to some embodiments;

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Figure 1:
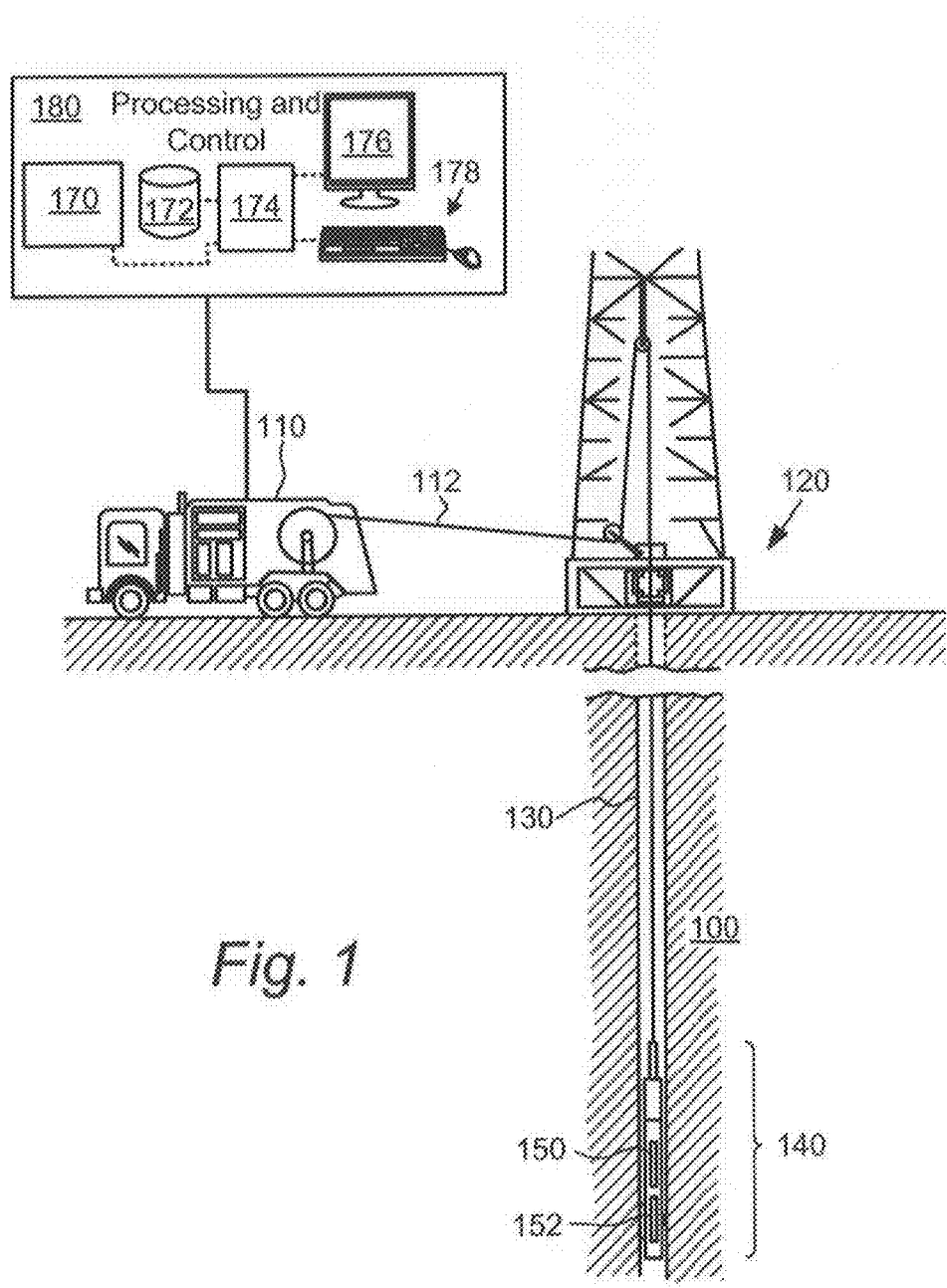
FIG. 1 shows a downhole focused sampling tool being deployed in a wellbore, according to embodiments.

FIG. 1 shows a downhole focused sampling tool being deployed in a wellbore, according to embodiments. Wireline truck 110 is deploying wireline cable 112 into well 130 via well head 120. Downhole sampling tool 140 is disposed on the end of the cable 112 in a subterranean formation 100. According to some embodiments downhole sampling tool 140 performs focused fluid extraction too using a dual flowline extraction probe module 152. For example, a focused fluid extraction tool using Schlumberger's Quicksilver Probe could be used. Tool 140 also preferably includes a downhole fluid analysis module 150. According to some embodiments, the data from the tool 140 can be recorded and/or processed downhole within tool 140, and/or can be transmitted to wireline truck 110 for recording and/or processing. According to embodiments, tool 140 is controlled locally with processing systems within tool 140 and/or from the surface using processing systems for example in wireline truck 110.

Processing system 180 can be located in wireline truck 110, at location near wellhead 120 or at a remote location. According to some embodiments, some or all of the functionality of processing system 180 can be located within sampling tool 140. Processing system 180 is to control, record and process data from sampling tool 140. Processing system 180 includes one or more central processing units 170, storage system 172, communications and input/output modules 174, a user display 176 and a user input system 178. Input/output modules 174 include modules to communicate with and control sampling tool 180.

FIGS. 2 and 3 illustrate features of a focused probe used for downhole fluid sampling, according to some embodiments. A focused sampling operation differs from a conventional sampling operation in equipment, technique, and results. Unlike conventional sampling which utilizes a single flowline and pump, focused sampling often makes use of dual flowlines. Referring to FIG. 2, focused probe 200 includes two concentric probes. The outer guard probe 212 surrounds the central fluid extraction probe 222. Each probe has an independent pump and separate flowline. Packers, including outer packer 210 and inner packer 220 surround and separate the probes 212 and 222 and seal against the borehole wall. FIG. 3 is a side view of probe 200 shown engaged against a borehole wall having a borehole wall 306. Although comingled contaminated fluid initially flows into both probes 212 and 222, in a short time, the flow is separated to draw filtrate 304 in to the guard flowline 314 and formation fluid 302 into the extraction line 324. The contamination level of the extracted fluid decreases quickly with time to an acceptable level.

Figure 4:
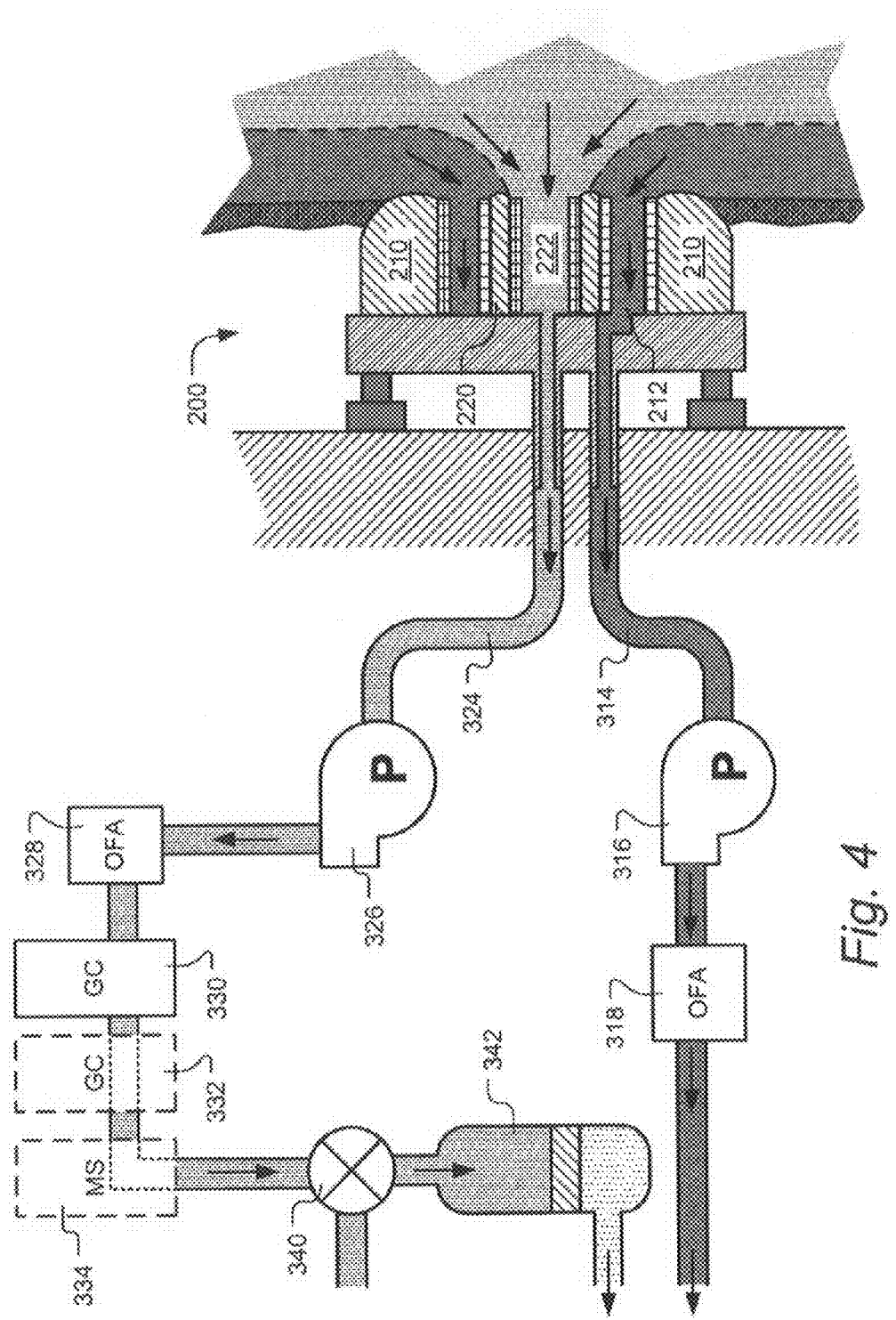
FIG. 4 is a block diagram schematically illustrating a focused extraction probe used in connection with downhole gas chromatographic and downhole mass spectrometry, according to some embodiments.

FIG. 4 is a block diagram schematically illustrating a focused extraction probe used in connection with downhole gas chromatographic and downhole mass spectrometry, according to some embodiments. In FIG. 4 probe 200 is engaged against borehole wall 306 such that formation fluid 302 flows into extraction line 324 and filtrate 304 flows into the guard flowline 314. Guard flowline 314 is serviced by pump 316 and extraction flowline 314 is serviced by pump 326. Separate pressure gauges, not shown, are also provided on each flow line 314 and 324. According to some embodiments the pumps 316 and 326 operate in a synchronized fashion. According to some embodiments, guard flowline 314 has an optical fluid analysis module 318 associated with it to analyze the fluid in the guard flowline 314. Similarly, the extraction flowline 324 has an optical fluid analysis module 328. The fluid analyzers 318 and 328, can be used, for example to monitor filtrate contamination on both the extraction and guard flowlines. Commingled flow may be achieved by connecting the extraction and the guard probe areas hydraulically. This functionality is controlled by a flowline seal valve, not shown, and emulates a conventional sampling probe but with greatly increased cross-sectional area at the sandface. Commingled flow is recommended for pretests, and also as the initial cleanup in some situations. The flow of formation fluid can be directed either down the flowline and out to the wellbore using the guard pump 316, or up the flowline using the sample extraction pump 326.

According to some embodiments, downhole gas chromatography module 330 and optionally a subsequent gas chromatography module 332 and/or mass spectrometry module 334. For further details on downhole mass spectrometry, refer to one or more of the following: U.S. Pat. No. 7,384,453; U.S. Pat. No. 7,600,413; U.S. Pat. No. 7,654,130; U.S. Pat. No. 7,637,151; U.S. Pat. No. 7,658,092; U.S. Patent Application Publ. No. US2009/0151426; U.S. Patent Application Publ. No. US2009/0158820; U.S. Patent Application Publ. No. US2009/0158815; U.S. Patent Application Publ. No. US2009/0150087; U.S. Patent Application Publ. No. US2008/0105032; U.S. Patent Application Publ. No. US 2009/0139934; and U.S. Provisional Patent Application Ser. No. 61/250,310, entitled "Micro-thermal conductivity detector, method to fabricate such and chromatography system using such." each of which is incorporated by reference herein.

According to some embodiments, 2D GC, or GC×GC, such as with modules 330 and 332 can be used to give detailed species specific compositional information for the extracted fluid in flowline 324. By using two GC modules or two-dimensional chromatography, accurate abundances of individual compounds can be obtained, and in some cases subtle reservoir non-heterogeneities such as biomarkers can be revealed. According to some embodiments, classes of compounds can be identified by two-dimensional chromatography through comparison of acquired data with a reference chromatogram from a different oil sample, for which prior identification has already been made. For example, 2D GC is useful in cases where the fluid has not been heavily biodegraded and still has a representative mix of aromatic and alkane features.

In cases of severely biodegraded reservoir fluids containing few n-alkanes, using only a single GC coupled to a flame ionization detector (FID) may not be sufficient. According to some embodiments, a downhole mass-spectrometer, such as with module 334, is be used for identification of unknown components in complex matrices. According to some embodiments, mass spectrometry module 334 is combined with a single gas chromatography module such as module 330 (GC×MS). According some other embodiments, mass spectrometry module 334 is combined with two gas chromatography modules 330 and 332 (GC×GC×MS).

The identification of more subtle reservoir non-heterogeneities, such as biomarkers can be very beneficial. For example, biomarkers and other subtle non-heterogeneities can be of use in analyzing reservoir connectivity and compartmentalization. Biomarkers are complex organic compounds composed of carbon, hydrogen, and other elements. They occur in sediments, rocks, and crude oils and show little or no change in structure from their parent organic molecules in living organism. Biomarkers are useful because their complex structure reveals information about their origin and geological history. Biomarker contributions include acyclic isoprenoids, such as pristane and phytane, as well as polycyclic alkanes including tricyclic terpanes, steranes and hopanes. Ratios specific biomarkers can be used to assess the burial history and source of sedimentary organic matter. Ratios describing the burial history of oil typically compare two or more stereo-isomers formed by the thermodynamic instability of a precursor molecule's exposure as it becomes exposed to increasing burial temperatures. Ratios assessing the source of the sedimentary organic matter that produced a given crude oil illustrate the relative abundance of various biomarkers derived from specific types of organisms, which are believed to be endemic to specific depositional environments.

Figure 5:
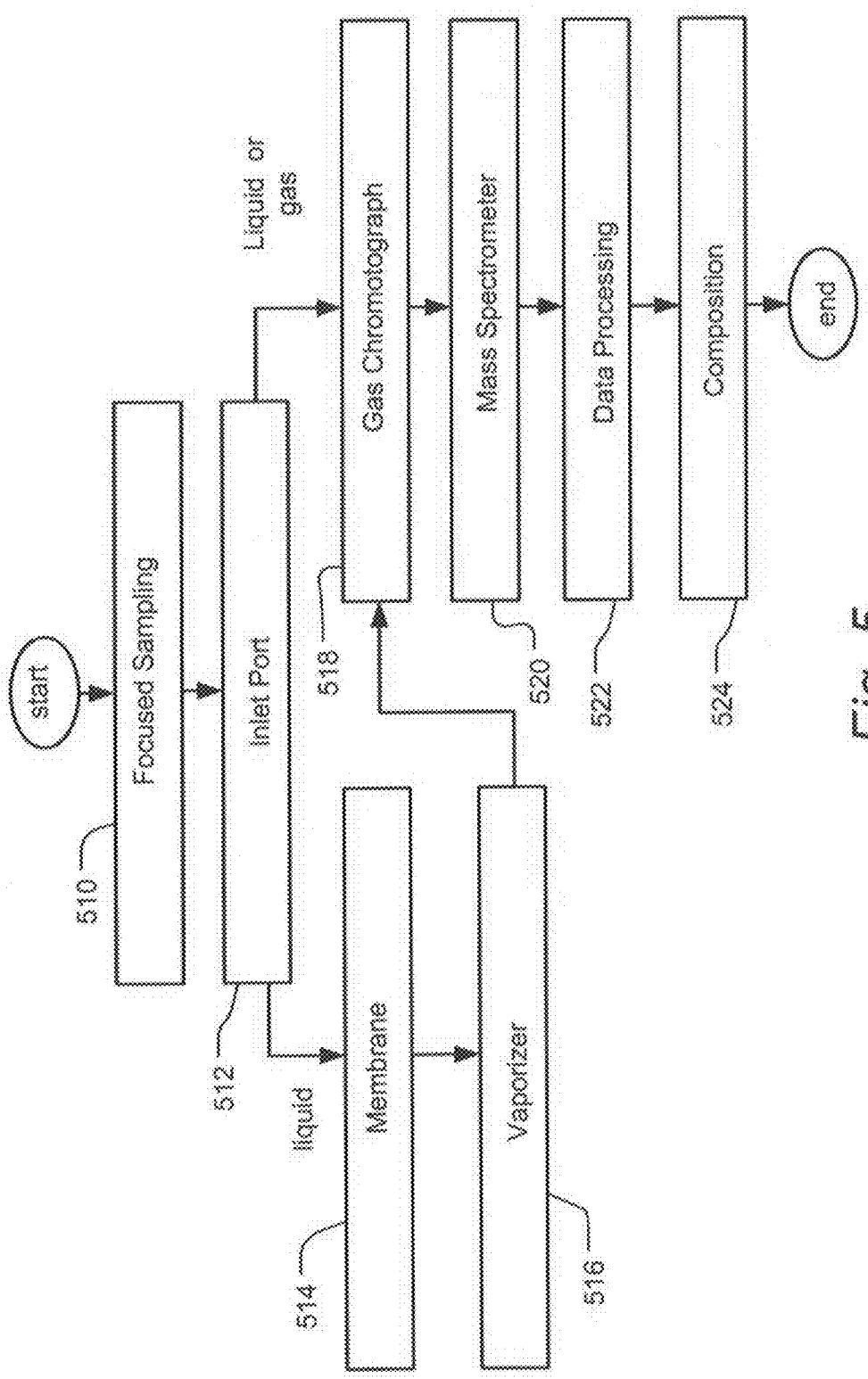
FIG. 5 is a flow chart illustrating steps of downhole fluid analysis using gas chromatography and mass spectrometry, according to some embodiments.

FIG. 5 is a flow chart illustrating steps of downhole fluid analysis using gas chromatography and mass spectrometry, according to some embodiments. In step 510 fluid extraction using focused sampling, such as using multi-flowline probe techniques as described with respect to FIGS. 1-3. In step 512, an inlet port includes taking the sample from the reservoir fluid extraction pressure, for example of 20K psi, to about 1 atmosphere (14.7 psi), where a gas chromatography system can operate. According to some embodiments, liquid samples are passed through a membrane in step 514 and a vaporizer in step 516. According to some other embodiments, liquid is injected directly into the gas chromatograph in step 518 where the liquid can be vaporized, for example using heat. In the case of gas samples, the gas is also injected into the gas chromatograph in step 518. According to some embodiments, the gas chromatography step 518 includes two gas chromatography columns are connected sequentially with a modulator positioned in between. According to some embodiments, in step 520 the sample is passed through a down-hole mass spectrometry module, as is described in further detail herein. In step 522 data processing is carried out to determine composition of the extracted fluid, which is yielded in step 524.

Figure 6:
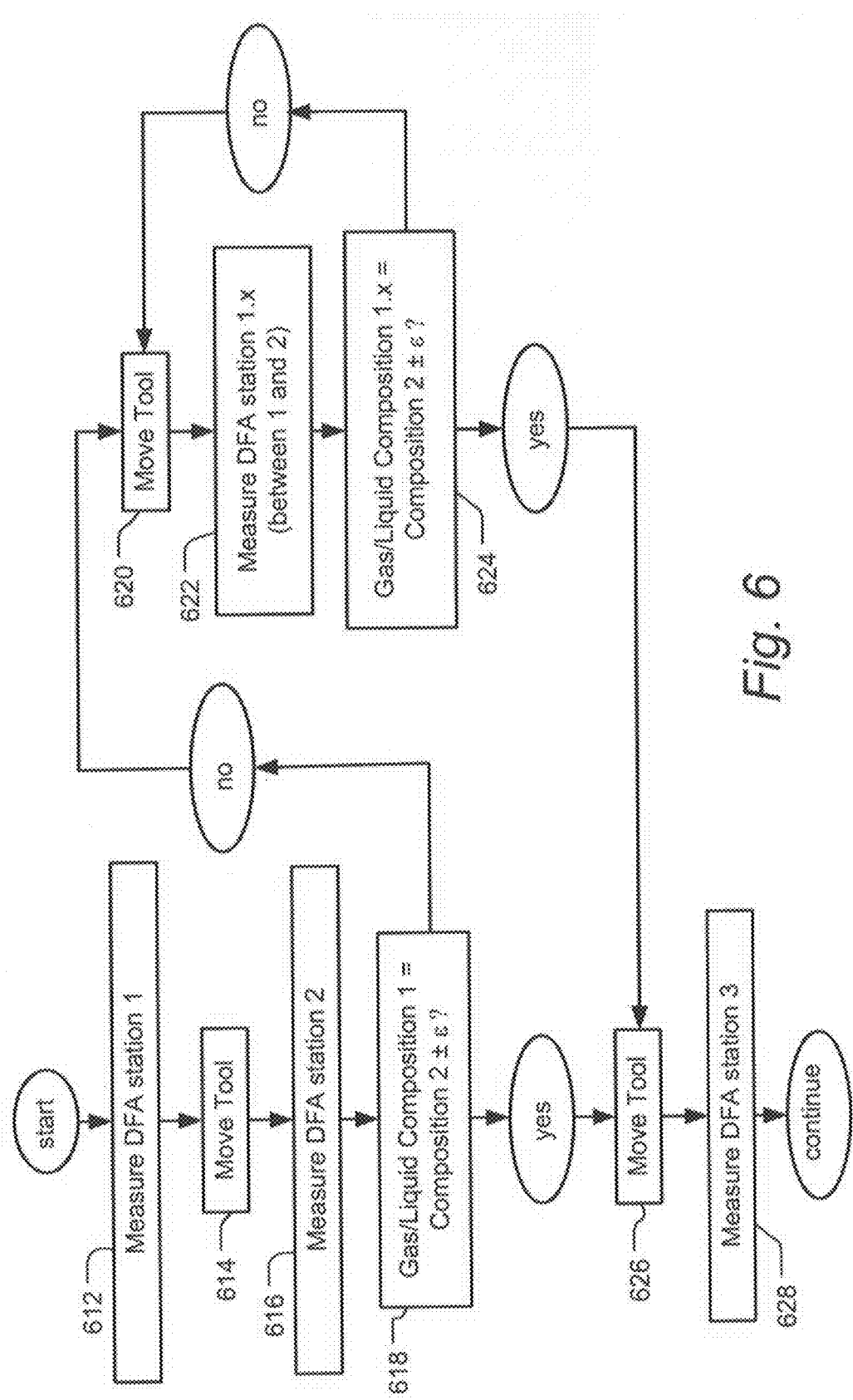
FIG. 6 is a flow chart illustrating steps of downhole fluid sampling with downhole fluid analysis, according to some embodiments.

FIG. 6 is a flow chart illustrating steps of downhole fluid sampling with downhole fluid analysis, according to some embodiments. In step 612, a downhole tool, such as shown in FIG. 1, and preferably capable of focused extraction such as with multiple flowlines, is positioned at a first station, "station 1," and a downhole fluid analysis is undertaken. According to some embodiments, the downhole fluid analysis such as described in FIGS. 4-5, in which the extracted fluid is analyzed using a GC, GC×GC, GC–MS, and/or GC×GC–MS. In step 614 the downhole tool is repositioned to a new location "station 2." In step 616, the downhole tool extracts and analyzes the fluid from location station 2. In step 618, a determination is made whether the composition of fluid extracted at station 1 is significantly different from the composition of fluid extracted at station 2. According to some embodiments, the comparison in step 618 is based on chromatographic and/or mass spectrometric analysis as is described herein. For example, the fluid analysis techniques described herein can be used to identify biomarkers or perform other forms of chemical "fingerprinting" to determine if the fluids from the station 1 and station 2 originate from different subterranean formations, sub-formations, or zones.

In step 620 if the compositional difference is significant, the downhole tool is moved back to a location "station 1.$x$" which is between station 1 and station 2 to extract a further sample. In step 622 the downhole tool extracts and analyzes the fluid from location station 1.$x$. In step 624, a determination is made whether the composition of fluid extracted at station 1.$x$ is significantly different from the composition of fluid extracted at station 2. If the fluid composition is significantly different, then in step 620 the tool is moved to a location between station 1.$x$ and station 2. In step 626 if the fluid composition is not significantly different between two stations than the tool is moved to a location that is not between the two stations. In step 628 further measurements are taken and the process continues until the depth interval of interest for the wellbore is covered. Using the compositional analysis and repositioning workflow shown in FIG. 6, time and expense can be saved when surveying an given depth interval while maintaining suitably high spatial resolution.

According to some embodiments, a significant compositional difference in the reservoir oil between stations 1 and 2 is a change in the composition of the oil that would occur in the vicinity of an oil water contact where biodegradation has occurred. As another example, if n-alkanes, cyclo-alkanes, isoprenoid alkanes, branched alkanes, benzenes, napthalenes, fluorenes, phenanthrenes, steranes and hopanes are detected by GC×GC at station 1 but at station 2 certain of these classes such as the n-alkanes and branched alkanes have disappeared, then the oil at station 2 is clearly shown to be of different geochemical origin and/or maturity than the oil at station 2. According to embodiments using a GC×GC×MS, a specific mass to charge may be utilized as the indicator of compositional difference, for example the M/Z=191 ion fragment, may be examined. If the trinor-18a-neohopane, and trinor-17a-hopane, norhopane, normoretane, hopane, gammacerane and homohopanes detected at station 1 sample are absent in station 2, it could indicate a difference in geochemical origin because hopanes are amongst the most stable biomarkers.

According to some embodiments, the compositional analysis includes comparing normalized peak volumes across n-C12 to n-C40 range. According to some embodiments the normalized peak volumes for one or more of the following classes can be used in the compositional analysis: Triaromatic Steranes and Benzohopanes, Hopanes, Steranes, Pyrenes, Flouranthenes, Phenanthrenes, Fluorenes, Napthalenes, Indenes, Tricyclic Alkanes and Alkylbenzenes, Bicyclic Alkanes, Monocyclic Alkanes and Acyclics and Saturated Alkanes and Paraffins. For further information on biomarkers and related analysis techniques, see: *Nanoaggregates of Asphaltenes in a Reservoir Crude Oil and Reservoir Connectivity*, S. S. Betancourt, et. al., Energy & Fuels 2009, Amer. Chem. Soc., 23, 1178-1188 (2009), which is incorporated by reference herein.

According to some embodiments, the compositional analysis method uses a form of multivariate analysis to elucidate the differences between the crude oils. Examples of such analysis methods include Partial Least Squares and Principal Component Analysis.

Figure 10:
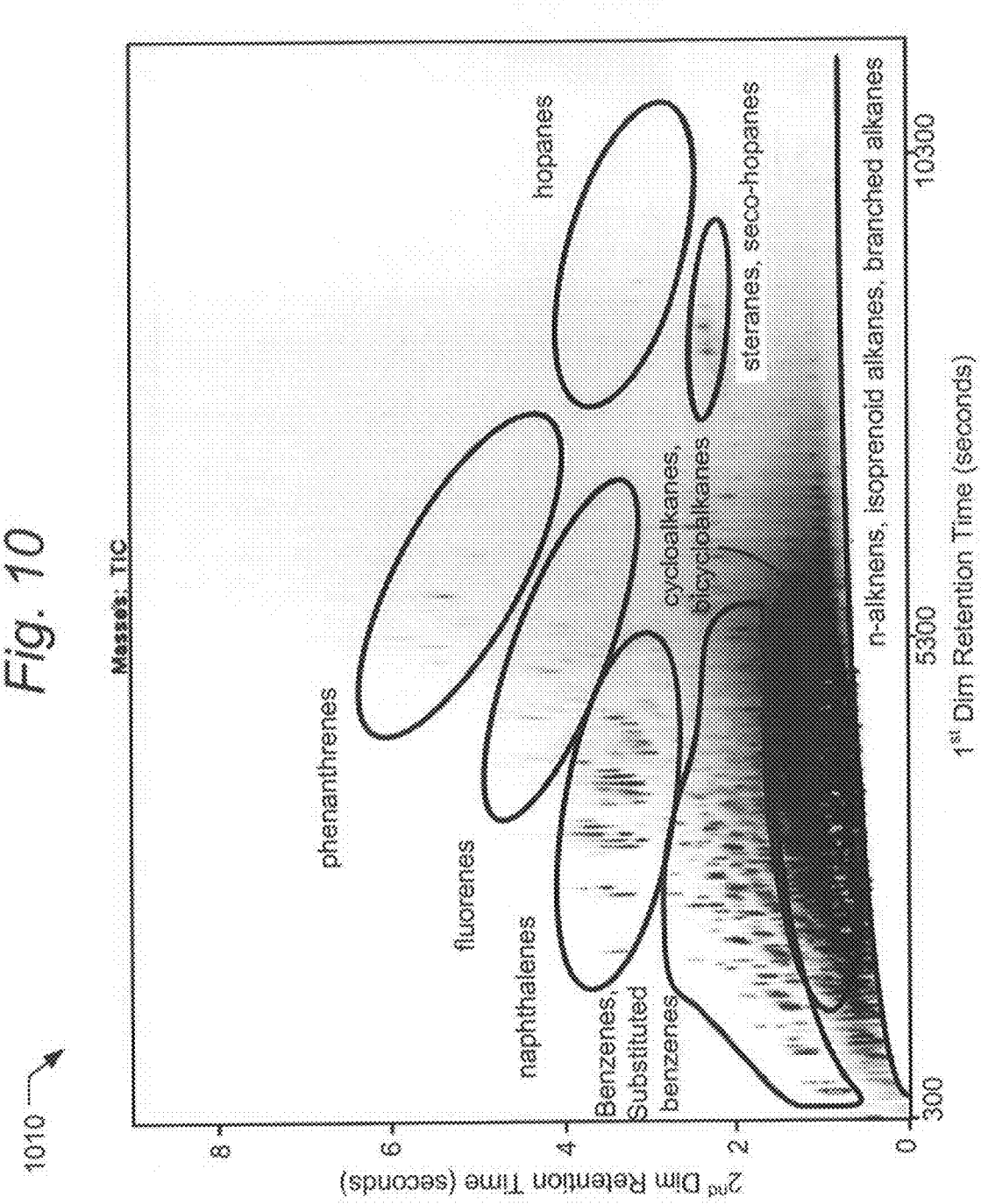
FIG. 10 is a plot showing two dimensional gas chromatography results of a typical reservoir fluid that has not been biodegraded, according to some embodiments.

FIG. 10 is a plot showing two dimensional gas chromatography results of a typical non-biodegraded reservoir fluid, according to some embodiments. In plot 1010 representative classes of compounds are labelled that are typically detected by GC×GC, for a crude oil that has not been biodegraded. Generally speaking, an M/Z slice could include any compounds in the 2D plot with a ion fragment at the particular mass to charge ratio.

According to some embodiments, when the techniques of FIG. 6 are combined with a focused probe, for example using a multi flowline guard probe arrangement, a synergistic generation of high spatial resolution of reservoir fluid composition in a short amount of time can be preformed.

Further detail as to downhole mass spectrometry will now be provided. Mass spectrometry (MS) is a standard laboratory technique that separates ions based on their mass-to-charge ratio, and measures the isotopic abundance. MS is used widely in the semiconductor and pharmaceutical industries for monitoring and identification and is critical in any vacuum environment for analyzing trace gases. Miniature MS systems have gone aboard the space shuttle and into marine environments.

Mass spectrometry can separately identify carbon numbers up to several hundred atomic mass units, as well as other reservoir gases such as CO2, N and H2S. A mass spectrometer is also ideal for measuring isotopic ratios of key biomarkers such as pristane/phytane which will aid identification of compartments.

According to some embodiments methods are described for determining the chemical composition of hydrocarbon mixtures in a downhole environment, including but not limited to the gases methane, ethane, propane, butane, pentane, hexane, heptane, C8+, N2, H2S and CO2. According to some embodiments, the isotope ratios C12/C13, O16/O18 and H1/H2 can also be determined using the technique of mass spectrometry for the analysis.

According to some embodiments, logging of isotope ratios and chemical compositions of gases, oils, and waters in real-time can be provided. The techniques described herein are an improvement over the conventional methods that require samples to be brought to surface facilities for analysis. According to some embodiments, an interpretation algorithm may depend on cross correlation with well log data obtained by other spectroscopic techniques. According to some embodiments, methods of sustaining high vacuum conditions in a downhole environment are described. According to some embodiments, methods of soft photo-ionization that produces a molecular ion are described.

Figure 7:
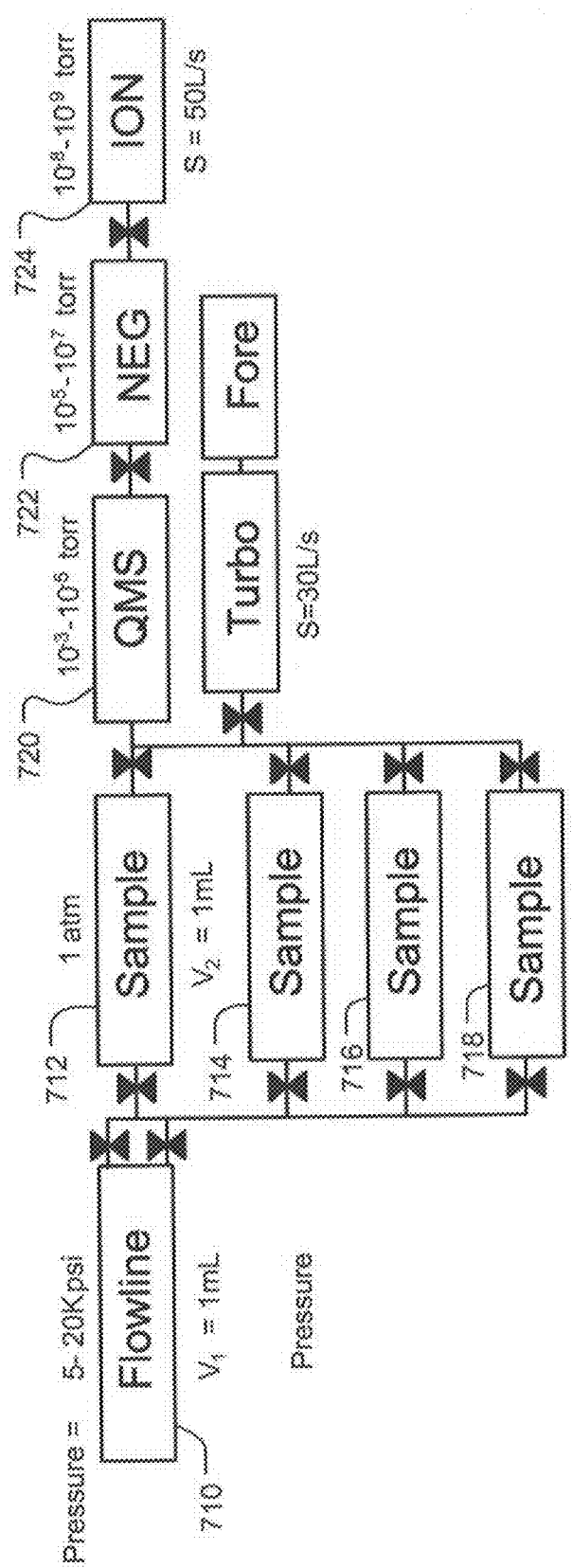
FIG. 7 is a block diagram illustrating certain aspects of a downhole mass spectrometry system, according to some embodiments.

FIG. 7 is a block diagram illustrating certain aspects of a downhole mass spectrometry system, according to some embodiments. A small volume of liquid is isolated from the flow line by means of electromechanical valves. Sample gases are allowed to expand into an evacuated chamber. According to some embodiments, sample gases are allowed into the measurement chamber through a piezoelectric leak valve. Sample ionization occurs either through electron impact or single photon dissociation using a He lamp. Mass selection is performed using a quadrupole (DC/RF) mass spectrometer. Detection is via a Faraday cup, measuring the ion current. Target chamber gases are pumped out with a combination of a non-evaporable getter pump and a sputter ion pump. Multiple sample expansion chambers are isolated from each other by a series of valves, and concentration is determined by solving a system of n linear equations for the components $H_M$.

Referring to FIG. 7, first a small quantity of the fluid is extracted from a flowline 710 via a sampling device. The quantity of fluid of gas extracted from the formation will on the order of a micro-liter. The liquid or gas is allowed to expand into a sample chamber 712 that is roughly one million times the volume of the extracted fluid. In one embodiment of the tool there are multiple sample chambers 712, 714, 716 and 718, which are isolated from each other by valves. After expansion a piezo-electric leak valve is opened into the ionization chamber where the sample gases are ionized either via photons or electrons. In quadraupole mass spectrometer (QMS) 720, the molecular ions or fragments travel into the quadrupole RF fields where they are filtered on the basis of their mass/charge ratio. As the mass spectrometer is scanned, the selected ions pass through to the detector, which consists of a Faraday cup. The vacuum is maintained by a combination of ion and non-evaporable getter pumps 722. The pumps are separately isolated from the main chamber by a series of valves. During data acquisition, either one or both of the NEG pumps 722 or ion pumps 724 may be open to the chamber 720 housing the detector. The MS detector is shielded from the magnetic fields generated by the ion pump.

Further detail regarding the vacuum system will now be described. Since mass spectrometers use the m/z ratio to separate constituents, the target molecule must be ionized. Charged particles loose energy through interactions with gas molecules. The distance between the source and detector dictates the maximum operating pressure at which the device can operate. For example, at a pressure of $10^{-3}$ ton the mean free path of an ion between collisions is about 5 cm, while at $P=10^{-5}$ ton, the mean free path grows to half a meter. Thus mass spectrometry uses moderate to high vacuum conditions. For a standard commercial QMS system, such as according to some embodiments, a vacuum of at least $P=10^{-5}$ ton or better is used at all times. According to some embodiments, this is achieved by a combination of two non-mechanical vacuum pumps working in tandem. The first of these is an ion pump 724, which may be of either the diode or the triode variety.

FIGS. 8A-B illustrate an ion pump for used in downhole mass spectrometry, according to some embodiments. In FIG. 8A, ion pump 800 has components adapted to the borehole geometry. A honeycomb array of anodes 814 arranged in a cylindrically symmetric pattern around the borehole, sandwiched by a pair of titanium cathode plates 812 and 816 on either side. The anode 814 is held at several kV. The cathodes 812 and 816 and anode 814 are sandwiched between a pair of permanent magnets 810 and 818 which have been shaped into a cylindrical geometry. The electric and magnetic fields are parallel inside the cells, so the ions travel in spiral paths and are trapped by sputtering on the cathode. FIG. 8B shows further detail of a portion of ion pump 800. The cathode/anode array are biased by a static electric field. The center region of the pump 820 is open to ensure high conductance and to accommodate one or more non-evaporable getter pumps. The pumping speed of this device is approximately 50 L/s/ft and it is of a modular design so that several units can be stacked end to end. The range of operation of this pump is for pressures between $10^{-5}$ and $10^{-9}$ ton.

According to some embodiments, a second type of pump can be used: a non-evaporable getter pump or NEG. The NEG pump does not require electrical power and continues pumping gases until the surface of the getter material is completely saturated by absorbates, at which point it must be reconditioned (up hole). The NEG pump does not pump hydrocarbons, so it can be operated during data acquisition without biasing the sample. The NEG pump is also used when the tool is being shipped to the field prior to a logging run.

During a logging run the ambient temperature in the borehole may be as high as 175 C. As a result, gases from the body of the tool will desorb from the walls and surfaces. The net pumping speed of the ion and NEG pumps must be adequate to handle this, and the cycling of the measurement chamber.

Further detail of ionization methods will now be described. According to some embodiments a commercially available quadrupole mass spectrometer is used for filtering and detection. The method of ionization can be either electron impact ionization (EI) or photon ionization (PI). In the EI technique, a high-energy electron dislodges electron from a bond, creating a radical cation:

$$CH_4 + e^- \rightarrow CH_4^+ + 2e^-$$

The electron energy is adjustable, however 70 eV yields the best sensitivity for the instrument, because it is the highest ionization cross section. It is much higher than the first ionization energy of most hydrocarbons. (See Table 2). The excess energy remaining leads to further fragmentation into daughter ions:

$$CH_4 \rightarrow CH_3 \rightarrow CH_2 \rightarrow CH$$

The fragmentation pattern can be represented a system of linear system of equations, one for each mass peak in the spectra:

$$H_M = \Sigma_g (S_g \alpha_{Mg}) P_g \qquad (1)$$

Where: $H_M$ is the total peak height at mass M; $S_g$ is the sensitivity factor for gas g: $S_g = (I_g - I_0)/(P_g - P_0)$; $\alpha_{Mg}$ is the fragmentation factor for gas g at mass M; and $P_g$ is the partial pressure of gas g.

The quantity Sg is determined by instrument calibration. The quantity $\alpha_{Mg}$ is determined by measuring the fragmentation pattern of a pure gas. The quantity is the current $H_M$ is measured at the detector. The partial pressures $P_g$ are determined by solving the n×m matrix using constrained non-negative least squares.

Figure 9:
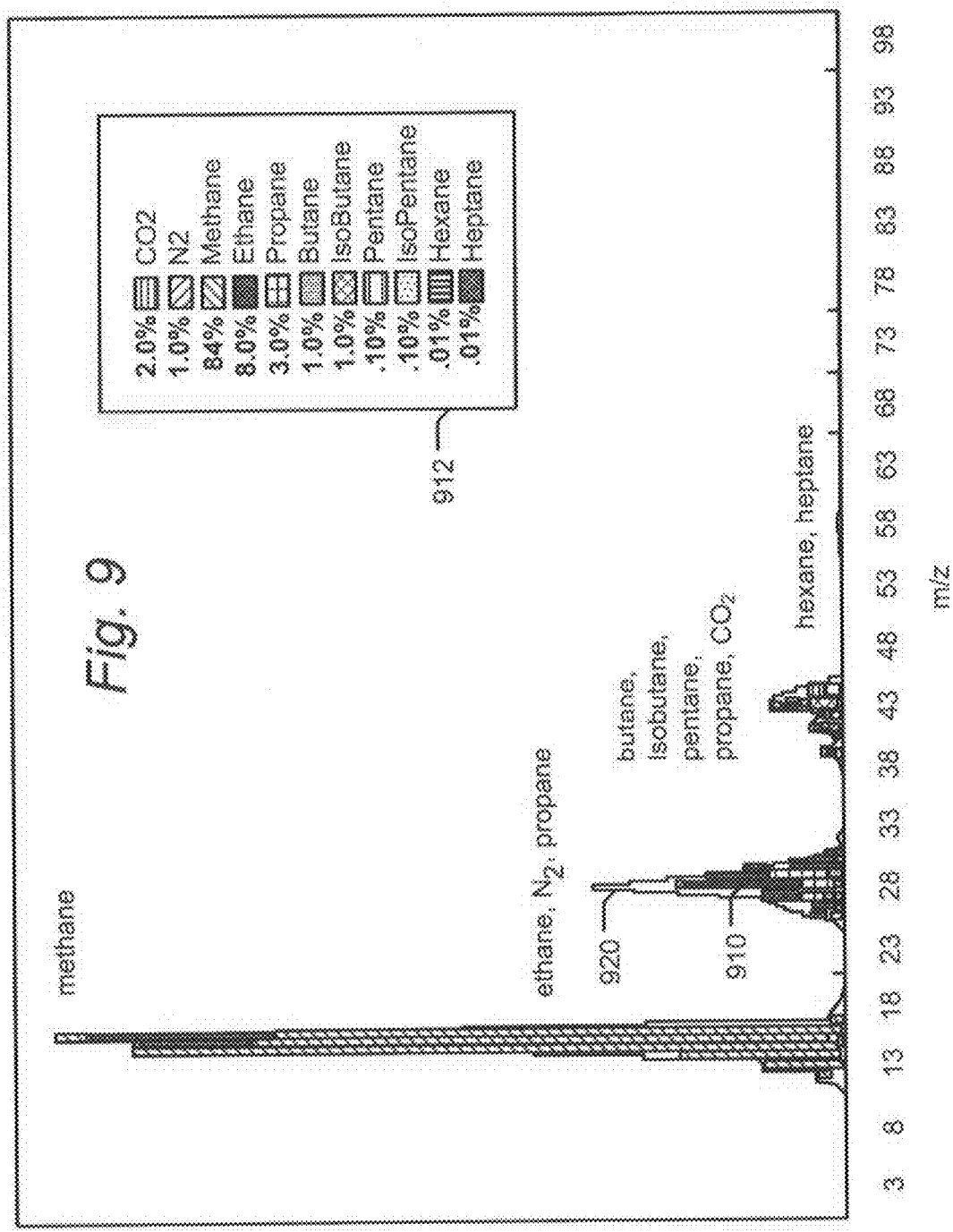
FIG. 9 is graph comparing measured data and predicted spectra, according to some embodiments.

Qualitative identification of formation fluids may be established by reference to a database of hydrocarbon mixtures. FIG. 9 is graph comparing measured data 920 and predicted spectra 910 based on NIST cracking patterns for quadrupole mass spectrometer using and electron ionization energy of 70 eV. Percentages of component gases are indicated in table insert 912.

An alternative is to use photons instead of electrons:

$$CH_4 + \lambda \rightarrow CH_4^+ + e^-$$

In PI the photon energy is much closer to the ionization threshold of the molecule so that one produces a high concentration of molecular ions with minimal fragmentation.

Table 2 gives the first ionization energies for selected hydrocarbons and other probable formation gases. The Helium I (21.22 eV) and Neon I (16.67 eV) resonance lines are both energetic enough to ionize all constituents of interest, however it is preferable to use the Helium one because the relative intensity is higher. If a closed photon source is employed, Argon (11.62 eV) can be employed with a LiF window. According to embodiments utilizing an ionization chamber, the electron and the photon sources are collocated.

The mass resolution is depends on the axial energy of the ions and is inversely proportional to the square of the driving frequency and the axial length of the quadrupole:

$$\Delta M_g = 4 \times 10^9 V_z / (fL_z)^2 \qquad (2)$$

Quadrupole and ion trap mass spectrometer offer a resolution 0.5-1 amu, which is sufficient to distinguish common isotopes, such as carbon $C^{12}$ and $C^{13}$ Other stable isotopes present in formation water include $H^2$ (Deuterium), $O^{18}$, $S^{34}$, $N^{15}$, $Cl^{37}$, $B^{11}$ and the radiogene isotopes $Sr^{87}$ and $Sr^{86}$.

According to some embodiments, the downhole mass spectrometry techniques described herein are coupled with a pre-filtering apparatus such as GC, GC×GC, and/or LC.

TABLE 2

Mass, base peak, number of fragments (EI only) and ionization energies for selected light ends and other common reservoir gases.

| Formula | Component | Mass (amu) | Base peak | Number fragments | Boiling point (° C.) | Ionization energy (eV) | Ionization Wavelength (nm) |
|---|---|---|---|---|---|---|---|
| $CH_4$ | Methane | 16 | 16 | 4 | −161 | 12.98 | 95.53 |
| $C_2H_6$ | Ethane | 30 | 28 | 13 | −89 | 11.65 | 106.44 |
| $C_3H_8$ | Propane | 44 | 29 | 21 | −44 | 11.07 | 112.01 |
| $C_4H_{10}$ | Butane | 58 | 43 | 28 | −0.5 | 10.63 | 116.65 |
| $C_5H_{12}$ | Pentane | 72 | 43 | 32 | 36 | 10.35 | 119.81 |
| $C_6H_{14}$ | Hexane | 86 | 57 | 32 | 68 | 10.18 | 121.81 |
| $C_7H_{16}$ | Heptane | 100 | 43 | 43 | 98 | 10.08 | 123.02 |
| $C_8H_{18}$ | Octane | 114 | 43 | 38 | 125 | 10.24 | 121.09 |
| $N_2$ | Nitrogen | 28 | 28 | 3 | −195.8 | 15.6 | 79.49 |
| $CO_2$ | Carbon Dioxide | 44 | 44 | 12 | −78.5 | 13.79 | 89.92 |
| $H_2S$ | Hydrogen Sulfide | 34 | 34 | 5 | −60.7 | 10.46 | 118.55 |

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method for surveying a formation, the method comprising:
    positioning a tool at a first location in a borehole, the tool including a downhole fluid analysis system;
    extracting a first sample of reservoir fluid while the tool is positioned at the first location;
    performing a compositional analysis of the first sample using the downhole fluid analysis system, wherein the compositional analysis includes identifying individual molecules having at least 10 carbon atoms;
    repositioning the tool to a second location in the borehole, wherein the second location is different from the first location;

extracting a second sample of reservoir fluid while the tool is positioned at the second location;

performing a compositional analysis of the second sample using the downhole fluid analysis system, wherein the compositional analysis includes identifying individual molecules having at least 10 carbon atoms;

comparing compositional analysis results of the first sample and the second sample using individual molecules having at least 10 carbon atoms;

repositioning the tool back to a third location that is within the borehole between the first location and the second location, wherein the repositioning depends at least in part on the comparison of the first sample and the second sample;

extracting a third sample of reservoir fluid while the tool is positioned at the third location; and performing a compositional analysis of the third sample using the downhole fluid analysis system, wherein the compositional analysis includes identifying individual molecules having at least 10 carbon atoms.

2. The method according to claim 1, wherein the compositional analysis includes identifying individual molecules having at least 20 carbon atoms.

3. The method according to claim 1, wherein the individual molecules comprise at least one biomarker.

4. The method according to claim 1, wherein the downhole fluid analysis system includes a downhole gas chromatography system.

5. The method according to claim 4, wherein the gas chromatography system is adapted to perform two-dimensional gas chromatography.

6. The method according to claim 1, wherein the downhole fluid analysis system includes a downhole mass spectrometry system.

7. The method according to claim 6, wherein the downhole mass spectrometry system includes an ion pump adapted for deployment in the borehole.

8. The method according to claim 6, wherein the downhole mass spectrometry system includes one or more non-evaporable getter pumps.

9. The method according to claim 1, wherein the extraction is made using a sampling probe having more than one flowline.

10. The method according to claim 9, wherein the more than one flowline includes a first flowline connected to a central probe portion and a second flowline connected to an outer guard portion surrounding the central probe portion.

11. The method according to claim 1, wherein the tool is a wireline tool.

12. The method according to claim 1, wherein the method is carried out during a drilling process.

13. The method according to claim 1, wherein the comparing process is performed using individual molecules having at least 10 carbon atoms to determine at least one of reservoir connectivity and reservoir compartmentalization.

14. The method according to claim 1, wherein the comparison of compositional analysis results between the first sample and the second sample is performed to determine whether there is a compositional difference between the first sample and the second sample and, when there is a compositional difference between the first sample and the second sample, repositioning the tool back to the third location that is within the borehole between the first location and second location.

15. The method according to claim 14, wherein the compositional difference indicates reservoir compartmentalization.

16. A system comprising:
a downhole fluid analysis system adapted to be deployed at a number of depth positions in a borehole and to analyze composition of extracted fluid samples by identifying individual molecules having at least 10 carbon atoms; and
a processing system programmed (i) to compare compositional analysis results from a first sample extracted from a first location and a second sample extracted from a second location that is different from the first location using individual molecules having at least 10 carbon atoms and (ii) to control repositioning of the tool back to a third location that is within the borehole between the first location and the second location depending at least in part on the comparison of the first sample and the second sample.

17. The system according to claim 16, wherein the analysis includes identifying individual molecules having at least 20 carbon atoms.

18. The system according to claim 16, wherein the individual molecules comprise at least one biomarker.

19. The system according to claim 16, wherein the downhole fluid analysis system includes a downhole gas chromatography system.

20. The system according to claim 19, wherein the gas chromatography system is adapted to perform two-dimensional gas chromatography.

21. The system according to claim 16, wherein the downhole fluid analysis system includes a downhole mass spectrometry system.

22. The system according to claim 21, wherein the downhole mass spectrometry system includes an ion pump adapted for deployment in the borehole.

23. The system according to claim 21, wherein the downhole mass spectrometry system includes one or more non-evaporable getter pumps.

24. The system according to claim 16, further comprising:
a focused probe member adapted to extract reservoir fluid samples, wherein the probe member has more than one flowline.

25. The system according to claim 24, wherein the more than one flowline includes a first flowline connected to a central portion of the probe member and a second flowline connected to an outer guard portion surrounding the central probe portion.

26. The system according to claim 16, further comprising:
a wireline tool that includes the downhole fluid analysis system.

27. The system according to claim 16, wherein the downhole fluid analysis system is adapted to be deployed as part of a drill string during a drilling process.

28. A method for surveying a formation, the method comprising:
(a) positioning a downhole sampling tool at a first location in a borehole, the downhole sampling tool including a downhole fluid analysis system;
(b) extracting a first sample of reservoir fluid while the downhole sampling tool is positioned at the first location;
(c) performing a compositional analysis of the first sample using the downhole fluid analysis system;
(d) repositioning the downhole sampling tool to a second location in the borehole, wherein the second location is different from the first location;
(e) extracting a second sample of reservoir fluid while the tool is positioned at the second location;

(f) performing a compositional analysis of the second sample using the downhole fluid analysis system;

(g) comparing compositional analysis results of the first sample and the second sample;

(h) repositioning the downhole sampling tool back to a third location that is within the borehole between the first location and the second location, wherein the repositioning depends at least in part on the comparison of the first sample and the second sample in process (g);

(i) extracting a third sample of reservoir fluid while the downhole sampling tool is positioned at the third location; and (j) performing a compositional analysis of the third sample using the downhole fluid analysis system.

29. The method according to claim 28, wherein the comparison of compositional analysis results in process (g) is performed to determine whether there is a compositional difference between the first sample and the second sample and, when there is a compositional difference between the first sample and the second sample, performing processes (h), (i), and j).

30. The method according to claim 29, wherein, when there is no compositional difference between the first sample and the second sample, repositioning the downhole sampling tool to a third location within the borehole that is not between the first location and second location.

31. The method according to claim 29, further comprising:

(k) comparing compositional analysis results of the third sample to at least one of the first sample and the second sample to determine whether there is a compositional difference between the third sample and at least one of the first sample and the second sample;

(l) when there is a compositional difference between the third sample and at least one of the first sample and the second sample, repositioning the downhole sampling tool to a fourth location that is within the borehole between the third location and said at least one of the first location and the second location.

32. The method according to claim 31, further comprising: repeating processes of repositioning, extracting and performing a compositional analysis for different locations until no compositional difference is determined.

33. The method according to claim 29, wherein the compositional difference indicates reservoir compartmentalization.

34. The method according to claim 28, wherein the downhole fluid analysis system comprises a downhole gas chromatography system.

35. The method according to claim 28, wherein the downhole fluid analysis system comprises a downhole mass spectrometry system.

* * * * *